United States Patent [19]

Spann

[11] 4,433,678
[45] * Feb. 28, 1984

[54] DISPOSABLE ORTHOPEDIC SUPPORT

[76] Inventor: Donald C. Spann, 5 Ferncreek Ct., Greenville, S.C. 29615

[*] Notice: The portion of the term of this patent subsequent to Jan. 23, 1996 has been disclaimed.

[21] Appl. No.: 312,537

[22] Filed: Oct. 19, 1981

Related U.S. Application Data

[60] Division of Ser. No. 5,495, Jan. 22, 1979, Pat. No. 4,327,714, which is a continuation in part of Ser. No. 780,761, Mar. 24, 1977, Pat. No. 4,135,504.

[51] Int. Cl.³ .............................................. A61F 3/00
[52] U.S. Cl. .................................. 128/80 A; 128/149
[58] Field of Search ................ 128/80 R, 80 A, 80 B, 128/80 C, 134, 68, 149, 87 R, 153

[56] References Cited

U.S. PATENT DOCUMENTS

| | | | |
|---|---|---|---|
| 2,492,920 | 12/1949 | Koster | 128/80 R |
| 2,911,657 | 11/1959 | Streeter | 128/149 |
| 3,256,879 | 6/1966 | Hipps | 128/149 |
| 3,511,233 | 5/1970 | Holy, Jr. | 128/149 |
| 3,568,671 | 3/1971 | Graham | 128/87 R |
| 3,901,228 | 8/1975 | Brown | 128/149 |
| 3,903,878 | 9/1975 | Spann | 128/149 |
| 4,041,940 | 8/1977 | Frankel et al. | 128/80 C |
| 4,135,504 | 1/1979 | Spann | 128/80 A |
| 4,186,738 | 2/1980 | Schleicher et al. | 128/153 |
| 4,327,714 | 5/1982 | Spann | 128/80 A |

*Primary Examiner*—C. W. Shedd
*Attorney, Agent, or Firm*—Ralph Bailey

[57] ABSTRACT

An abduction pillow is illustrated wherein a wedge shaped body is constructed of synthetic foam material for positioning the legs of a patient in cushioned but fixed divergent position in which various parts of the abduction pillow are made to be disposable and wherein the wedge shaped body may be truncated to provide a space adjacent the patient's pelvic area which facilitates the placement and removal of catheter and drainage tubing and other related items which need be inserted in the body of the patient during and after surgery.

6 Claims, 4 Drawing Figures

DISPOSABLE ORTHOPEDIC SUPPORT

This application is a division of Ser. No. 005,495, filed Jan. 22, 1979, now U.S. Pat. No. 4,327,714, which is a continuation in part of Ser. No. 780,761, filed Mar. 24, 1977, now U.S. Pat. No. 4,135,504.

BACKGROUND OF THE INVENTION

Abduction pillows heretofore utilized were relatively rigid and covered with an air impervious plastic material. Such abduction pillows offered rigidity and failed to sufficiently depress or flex at the pressure points exerted thereon by the limbs. Since the surface of former abduction pillows is relatively smooth, the limbs tended to move or slide thereon rather than remain completely immobilized.

It has been found that with resilient abduction pillows made heretofore from synthetic foam materials such as in applicant's U.S. Pat. No. 4,135,504, that problems were encountered in sterilizing the product so that it may be reused. In particular, protein matter deposited on the abduction pillow from contact with the body of the patient is not capable of being sterilized such as body hair and attempts at removal often result in plucking of the foam material. Drainage from the patient's body and other residue such as dead cell material often stain the wedge shaped body of the pillow rendering it undersirable for further use. Furthermore, with prior abduction pillows, it has been found that inadequate space is provided between the patient's pelvic area and the top of the pillow making it awkward to route catheter and drainage tubing required during and after certain types of orthodpedic surgery.

Accordingly, it is an important object of this invention to provide an abduction pillow constructed of foam material which will minimize discomfort and injury to the user at the pressure points and may be readily reused by providing a disposable replacement outer cover for the contacting surface of the pillow.

Yet another important object of the present invention is to provide an abduction pillow constructed of foam material for use in orthopedic operations having a wedge shaped body and an apex portion removable to truncate the wedge shaped body to create a space between the wedge shape body and the pelvic area which facilitates the placement and removal of apparatus inserted in the patient's body during and after surgery such as tubing and the like.

SUMMARY OF THE INVENTION

It has been found that an improved abduction pillow can be provided having disposable parts which enhance its reusability while enhancing the dispersion of pressure on the inside knee area of the patient's leg. Furthermore, it has been found that an abduction pillow having disposable parts can be provided according to the invention wherein an apex portion of the abduction pillow may be removed to provide a truncated form for the main wedge shaped body portion of the pillow to create a space between the pillow and the patient's pelvic area for accommodating tubing and medical instrumentation required to be inserted in the patient both before and after orthopedic surgery.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
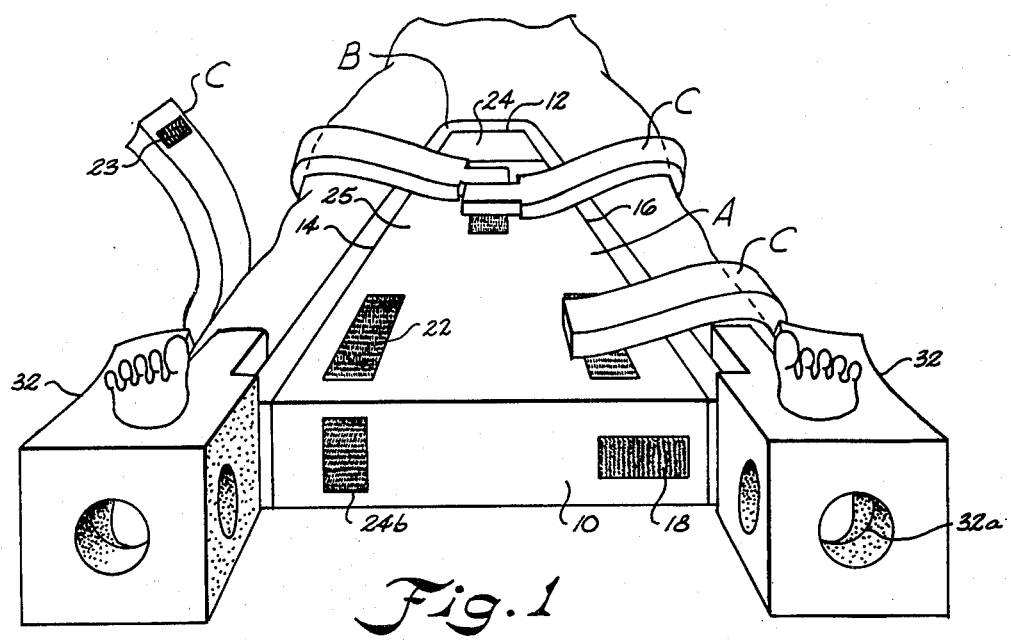
FIG. 1 is a perspective view illustrating an abduction pillow constructed in accordance with the present invention positioning the limbs of an orthopedic patient.

The drawing illustrates an abduction pillow for immobilizing the lower limbs of orthopedic patients including a flat wedge shaped body A constructed of synthetic foam material tapering outwardly at opposite sides. The wedge shaped body is of uniform thickness and of substantially rectangular cross-section. An elongated outer cover strip B of synthetic foam is removably carried about opposite sides and the upper end of wedge shaped body A assuming the divergent shape thereof and facilitating reuse of said wedge shaped body. Spaces strapping C is constructed of flat substantially rectangular strips of synthetic foam material extending about spaced portions of each limb fixing the same against the outer cover strip at respective sides of the wedge body maintaining the limbs in divergent fixed positions corresponding to the divergent disposition of the sides.

Figure 2:
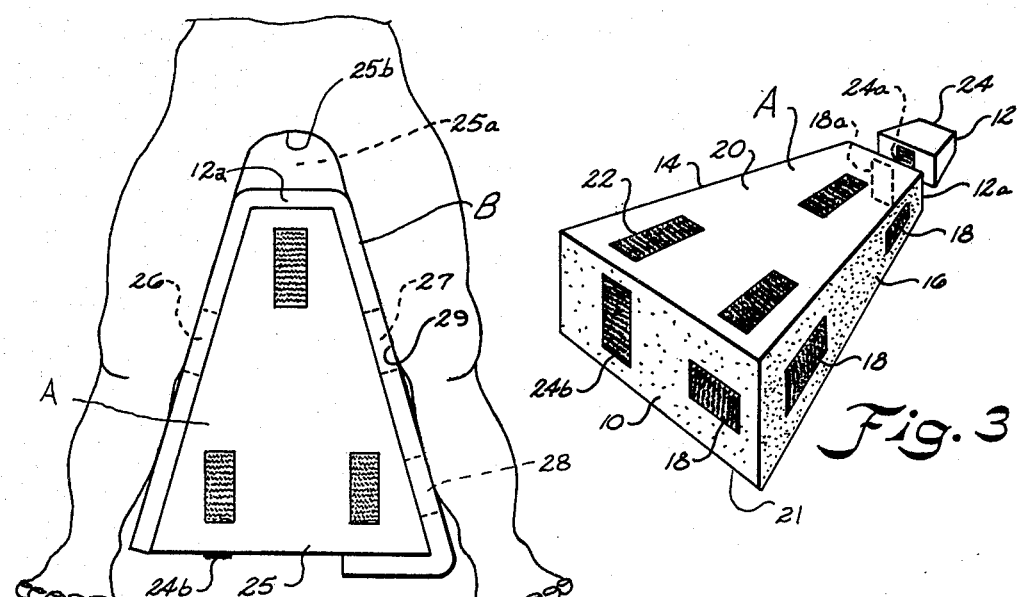
FIG. 2 is a top plan view illustrating an abduction pillow having a truncated wedge shaped body constructed in accordance with the invention.
Figure 3:
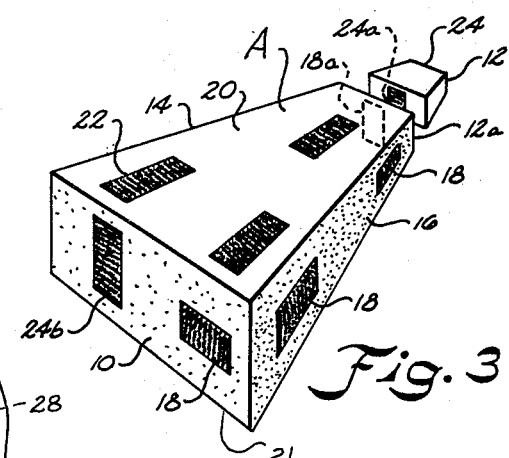
FIG. 3 is a perspective view further illustrating the wedge shaped body with apex portion removed for truncation.
Figure 4:
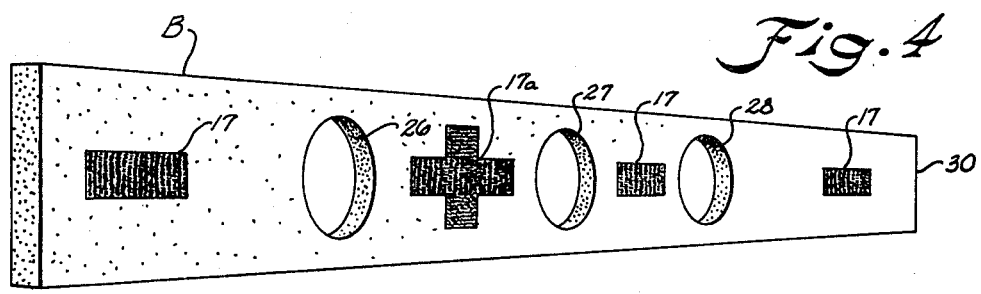
FIG. 4 is a perspective view illustrating a disposable outer cover strip for an abduction pillow constructed according to the invention.

Referring more particularly to FIGS. 1 through 3, it will be noted that the wedged shaped body A is defined in configuration by a first end 10 widened with respect to a second end 12 and a pair of diverging sides 14 and 16 which diverge outwardly from the end 12 for maintaining the limbs in diverging position as is desirable, for example, following surgery for replacing the hip joints. Connecting means in the form of Velcro tape strips are provided for attaching the cover strip B to the wedge body A. Strips 17 are carried at spaced positions on the cover strip B and strips 18 at spaced locations on the sides 14 and 16 and strip 18a at a truncated end 12a of the wedge body. Strip 17a is adapted for connection to vertical strip 18a as well as horizontal strip 18 carried on side 14 (not shown) for the purpose of which will become fully apparent hereinafter. With the cover strip B wrapped about and attached to the wedge shaped body, the strip assumes the shape thereof and the patient's legs bear against the cover strip at the respective sides 14 and 16 maintaining the limbs in proper divergent position. The Velcro tape strips may be affixed to the various members by suitable means such as gluing.

The wedge shaped block A has a front face 20 and back face 21 which have Velcro strips 22 positioned at like spaced points for fastening the strapping C. The strapping C is constructed of elongated relatively wide strips which are provided with fastening means in the form of complimentary Velcro tape strips 23 at inner end portions thereof so as to enable the strap ends to be fastened thereto with the body portion of the straps passing about the limbs of the patient and the front and back of the abduction pillow.

Since the pillow offers full support from the pelvic area all the way to the ankle, total support facilitating turning of the patient is provided. The pillow is cut to provide proper abduction or angular separation of the legs when bottom end 10 is placed adjacent the ankle portion.

As illustrated in FIGS. 1 and 3, wedge body A includes a removable apex dportion 24 at the end 12 thereof. Attachment means for integrally attaching the apex portion is provided in the form of Velcro strips 24a and 18a carried on respective mating surfaces whereby removal of the apex portion causes the wedge body to be truncated and shortened with respect to the location of the bottom end 10 being fixed adjacent the ankle portion of the leg so that the spread angle of the legs is maintained. Truncation results in the second end 12 of the wedge body A becoming at 12a. It will be noted that the apex portion 24 and the truncated wedge body 25 are both wedge shape having sides which diverge in linear alignment whereby integration of the two represents the single wedge shaped body A. The truncated wedge body shown as 25 provides a void space 25a between end 12a of the wedge body, and hence attached cover strip B, and the patient's pelvic or pubic area 25b which accommodates and facilitates the placement and removal of tubing and instrumentation required to be inserted in the patient's body before and after orthopedic surgery.

It has been found that the truncated wedge body and resulting void space 25a and the provision of disposable cover strip B reduce spoilage of the main body portion for certain types of orthopedic surgery where drainage is more pronounced thus facilitating reuse of the wedge body as well as routing and insertion of attendant tubing and apparatus. Other types of surgery do not require the void space and, in such cases, apex portion 24 may be left integrally attached as best shown in FIG. 1. Velcro strip 24b facilitates storage of the apex portion 24 when not in use or during shipping. Apex portion 24 may be disposed of and replaced since this area of the wedge body A is most susceptible to spoilage, further enhancing reuse of main wedge body 25.

Pressure dispersion means are provided in the form of apertures 26, 27 and 28 formed at spaced locations along the length of strip B for relieving and dispersing pressure exerted in the knee area of the patient's leg such as at 29 which represents the peroneal nerve area which is highly susceptible to excessive pressure which can result in paralysis and other temporary and permanent damage. It is noted that apertures 26 and 27 will be in pressure dispersing alignment with the knee area when the wedge body is utilized in truncated form and that apertures 26 and 28 will assume this alignment when strip B is wrapped about the wedge body with apex portion 24 in place. Velcro tape strip 18 carried on bottom end 10 and strip 17 carried next adjacent free end 30 of strip B cooperate to provide affixing means which secure the un-needed length of strip B to end 10 when wrapped about wedge body A in truncated form as best shown in FIG. 2.

Optional foot support blocks 32 may be utilized as desired which are constructed of synthetic foam material and have an internal cavity 32a therein carried adjacent a lower corner of said wedge shaped body for receiving and supporting the foot and ankle portions of the limbs.

It is thus seen that an orthopedic support has been provided for properly positioning the legs in an abducted position and which permits the patient to be turned in the bed or positioned on the side while the limbs are supported and fixed against rotation. A continuous support is provided for the full length of the limb and the support may be readily personalized to suit individual patients. The device is inexpensive and the disposable outer cover strip B is designed for one patient use for the duration of treatment, although it may be readily autoclaved, enhancing the reusability of the center wedge body. The wedge shaped body maintaining the legs in a properly spread position may be truncated to provide a space adjacent the pelvic area facilitating the routing and insertion of catheter tubing and the like without changing the angle of abduction.

While a preferred embodiment of the invention has been described using specific terms, such description is for illustrative purposes only, and it is to be understood that changes and variations may be made without departing from the spirit or scope of the following claims.

What is claimed is:

1. An abduction pillow for immobilizing the lower limbs of orthopedic patients comprising:
    a wedge shaped body defined by first and second ends, first and second sides extending between said first and second ends, said first end being widened relative to said second end whereby said first and second sides diverge away from said second end;
    a removable elongated outer cover strip of synthetic foam material carried about said first side, said second end, and said second side generally assuming said divergent shape of said wedge shaped body;
    connecting means carried at spaced positions on said outer cover strip and said wedge shaped body releasably attaching said outer cover strip to said wedge shaped body;
    spaced strapping constructed of flat substantially rectangular strips of synthetic foam material extending about spaced portions of each limb fixing same against said outer cover strip at respective sides of said wedge shaped body, said wedge shaped body between said cover strip and said sides maintaining said limbs in divergent fixed positions corresponding to the divergent disposition of said sides;
    fastening means carried at spaced positions on said wedge shaped body and on one side adjacent the ends of said strapping; and
    said fastened strapping cooperating with said wedge body so that said limbs may be secured at spaced locations therealong for immobilizing the limbs in spread position.

2. The apparatus of claim 1 wherein said outer cover strip includes pressure dispersion aperatures formed at spaced locations which align with the knee area of said limbs when connected about said wedge shaped body, said apertures serving to disperse and reduce pressure against said knee area when strapped thereagainst.

3. The apparatus of claim 1 wherein said wedge shaped body is constructed of synthetic foam material.

4. An abduction pillow for immobilizing the lower limbs of an orthopedic patient comprising:

a wedge shaped body having a thickness and configuration defined by first and second ends and first and second sides diverging outwardly from said second end terminating at said first end;

an elongated outer cover strip of synthetic foam material adapted for being removably fastened to said wedge shaped body and wrapped about at least a portion of said first and second sides and said second end facilitating reuse of said wedge shaped body; and means extended about the legs of the patient and fastened to said wedge shaped body fixing said legs against said outer cover strip at respective sides of said wedge shaped body, said wedge shaped body between said outer cover strip and said sides maintaining said legs in divergent fixed positions corresponding generally to the divergent configuration of said sides.

5. The apparatus of claim 4 wherein said elongated outer cover strip includes pressure dispersion means at space locations along the length thereof for relieving and dispersing pressure on the knee portion of the patient's legs when fixed thereagainst.

6. The apparatus of claim 4 wherein said wedge shaped body is constructed of synthetic foam material.

* * * * *